United States Patent
Orczy-Timko et al.

(10) Patent No.: US 10,662,939 B2
(45) Date of Patent: May 26, 2020

(54) SURGICAL FLUID MANAGEMENT SYSTEM

(71) Applicant: Cirrus Technologies Ltd., Budapest (HU)

(72) Inventors: Benedek Orczy-Timko, Budapest (HU); Csaba Truckai, Saratoga, CA (US)

(73) Assignee: Cirrus Technologies Ltd., Budapest (HU)

( * ) Notice: Subject to any disclaimer, the term of this patent is extended or adjusted under 35 U.S.C. 154(b) by 206 days.

(21) Appl. No.: 15/881,103

(22) Filed: Jan. 26, 2018

(65) Prior Publication Data

US 2019/0030235 A1    Jan. 31, 2019

Related U.S. Application Data

(60) Division of application No. 15/090,500, filed on Apr. 4, 2016, now Pat. No. 9,907,901, which is a
(Continued)

(51) Int. Cl.
   *F04B 43/12*   (2006.01)
   *F04B 43/00*   (2006.01)
   (Continued)

(52) U.S. Cl.
   CPC ...... *F04B 43/1292* (2013.01); *F04B 43/0081* (2013.01); *F04B 43/086* (2013.01);
   (Continued)

(58) Field of Classification Search
   CPC ............ A61M 2205/12; A61M 3/0266; A61M 2205/3393; A61M 1/0058; A61M 3/0283; A61M 2205/3331; F04B 43/1253; F04B 43/0072; F04B 43/0081; F04B 43/1284; F04B 43/086; F04B 43/1223; F04B 43/1261; F04B 43/1292; G01G 19/16;
   (Continued)

(56) References Cited

U.S. PATENT DOCUMENTS 3,723,030 A    3/1973    Gelfand
4,824,339 A    4/1989    Bainbridge et al.
(Continued)

FOREIGN PATENT DOCUMENTS

WO    WO-2016161060 A1    10/2016

OTHER PUBLICATIONS

International Search Report dated Jun. 23, 2016 for PCT Application No. US2016/25146.
(Continued)

*Primary Examiner* — Nathan C Zollinger
(74) *Attorney, Agent, or Firm* — Wilson Sonsini Goodrich & Rosati

(57) ABSTRACT

A fluid management system includes a disposable cassette carrying inflow and outflow tubing sections that are configured for releasably mating with a console including a control unit and a pair of roller pump heads. The console may automatically identify the disposable cassette and weigh the fluid in an inflow source. During operation, the system can monitor pressure in the working space, and provide for inflow and outflow control to maintain any desired operating parameters.

21 Claims, 13 Drawing Sheets

Related U.S. Application Data continuation of application No. PCT/US2016/025146, filed on Mar. 31, 2016.

(60) Provisional application No. 62/155,373, filed on Apr. 30, 2015, provisional application No. 62/142,694, filed on Apr. 3, 2015.

(51) Int. Cl.
    | | |
    |---|---|
    | *F04B 43/08* | (2006.01) |
    | *F04B 53/16* | (2006.01) |
    | *A61B 1/00* | (2006.01) |
    | *A61M 3/02* | (2006.01) |
    | *G01G 19/16* | (2006.01) |

(52) U.S. Cl.
    CPC ............ *F04B 53/16* (2013.01); *A61B 1/00119* (2013.01); *A61M 3/0266* (2013.01); *A61M 2205/12* (2013.01); *A61M 2205/3331* (2013.01); *A61M 2205/3393* (2013.01); *G01G 19/16* (2013.01)

(58) Field of Classification Search
    CPC ............ A61B 1/00147; A61B 1/00119; A61B 1/00133; A61B 1/015
    See application file for complete search history.

(56) References Cited

U.S. PATENT DOCUMENTS

| | | | |
|---|---|---|---|
| 5,380,173 | A | 1/1995 | Hellstrom |
| 5,431,626 | A | 7/1995 | Bryant et al. |
| 5,441,636 | A | 8/1995 | Chevallet et al. |
| 5,460,490 | A | 10/1995 | Carr et al. |
| 5,679,245 | A | 10/1997 | Manica |
| 5,720,721 | A * | 2/1998 | Dumas ............ A61M 5/16854 604/118 |
| 5,800,383 | A * | 9/1998 | Chandler ............ A61M 31/00 604/35 |
| 6,419,466 | B1 | 7/2002 | Lowe et al. |
| 6,523,414 | B1 | 2/2003 | Malmstrom et al. |
| 6,752,777 | B1 | 6/2004 | Takagi et al. |
| 7,121,143 | B2 | 10/2006 | Malmstrom et al. |
| 7,186,231 | B2 | 3/2007 | Takagi et al. |
| 7,556,611 | B2 | 7/2009 | Kolenbrander et al. |
| 8,403,875 | B2 | 3/2013 | Peters et al. |
| 8,708,943 | B2 | 4/2014 | Caleffi et al. |
| 8,840,581 | B2 | 9/2014 | McGill et al. |
| 8,888,738 | B2 | 11/2014 | Gillespie, Jr. et al. |
| 9,592,332 | B2 | 3/2017 | Guenther et al. |
| 2005/0118048 | A1* | 6/2005 | Traxinger ............ A61M 1/0058 417/477.2 |
| 2007/0098579 | A1* | 5/2007 | Boukhny ............ A61M 1/0031 417/477.2 |
| 2008/0112828 | A1 | 5/2008 | Muri et al. |
| 2008/0114289 | A1 | 5/2008 | Muri et al. |
| 2008/0114291 | A1 | 5/2008 | Muri et al. |
| 2010/0076372 | A1 | 3/2010 | Hacker et al. |
| 2011/0300010 | A1* | 12/2011 | Jarnagin ............ A61B 17/3207 417/477.2 |
| 2013/0131585 | A1 | 5/2013 | Eubanks et al. |
| 2013/0267892 | A1 | 10/2013 | Woolford |
| 2015/0335806 | A1 | 11/2015 | Rada et al. |
| 2016/0287779 | A1 | 10/2016 | Orczy-Timko et al. |

OTHER PUBLICATIONS

"Notice of Allowance dated Oct. 23, 2017 for U.S. Appl. No. 15/090,500".
Office action dated Feb. 7, 2017 for U.S. Appl. No. 15/090,500.
Office action dated Aug. 10, 2017 for U.S. Appl. No. 15/090,500.
U.S. Appl. No. 15/386,887 Office Action dated Aug. 23, 2017.

* cited by examiner

SURGICAL FLUID MANAGEMENT SYSTEM

CROSS-REFERENCE TO RELATED APPLICATIONS

This application is a divisional of U.S. patent application Ser. No. 15/090,500 filed Apr. 4, 2016, now U.S. Pat. No. 9,907,901, which is a continuation of International Patent Application No. PCT/US16/25146 filed Mar. 31, 2016, which claims priority from provisional application No. 62/155,373 filed on Apr. 30, 2015, and from provisional application No. 62/142,694 filed on Apr. 3, 2015, the full disclosures of which are incorporated herein by reference.

BACKGROUND OF THE INVENTION

1. Field of the Invention

The present invention relates to a fluid management system of the type used, for example, in endoscopic procedures.

Surgical fluid management systems typically deliver a fluid, such as saline, to a targeted working space or body cavity to provide access and visibility to the physician performing a procedure in the space. The fluid usually provides pressure sufficient to "open" the space (i.e. create a working space for the procedure) and additionally will usually flush blood and debris from the space.

Surgical fluid management systems are often inconvenient to use, difficult to monitor, and time-consuming to arrange. It would therefore be beneficial to provide improved surgical fluid management systems that overcome at least some of these shortcomings.

2. Background Art

Surgical fluid management systems are described in U.S. Patent Publications 2013/0267892 and 2010/0076372.

SUMMARY OF THE INVENTION

In general, the fluid management system includes a disposable cassette carrying inflow and outflow tubing sections that are configured for releasably mating with a control unit and roller pump heads. The fluid management system is adapted to automatically recognize the type of disposable cassette and the volume of fluid in an inflow source. During operation, the system can monitor pressure in the working space, and provide for inflow and outflow control to maintain any desired operating parameters. Other features, objects, and advantages will be apparent from the description and drawings, and from the claims.

The present invention provides improved fluid management systems and methods for their use. In particular, the present invention provides disposable tubing cassettes, consoles for detachably receiving the disposable tubing cassettes, and methods for mounting and replacing the tubing cassettes on the consoles. The disposable tubing cassettes will usually include first and second flexible tubes, where the first tube is used for delivering fluid from a fluid source to a patient and the second tube is used for removing fluid from the patient and delivering the fluid to a disposal receptacle. The tubing cassettes will typically also have a unitary construction such that the cassette can be roved from and replaced onto the console as a single unit. The unitary cassettes will typically be disposable after a single use, but in other embodiments the cassettes might be "resposable" with the flexible tubes being replaceable and the remaining portions of the cassette being serializable and reusable. By providing the first and second tubes in a single cassette, and having first and second rotors on a single rotor console, replacement of the tubes and arranging the fluid management system for a new patient is greatly facilitated. In addition, the fluid management systems of the present invention will provide capabilities for automatic loading of the cassette on to the console, typically using motorized loading mechanisms. The fluid management systems may also be configured to alert the user when the cassette has been successfully loaded or, conversely, when the cassette has not been successfully loaded. Further capabilities include sensing conditions of the fluid, particularly pressure being delivered from the fluid source or in some cases being removed from the patient. Automatic locking capabilities may also be provided by the console.

In a first specific aspect, the present invention provides a disposable cassette for use with a surgical fluid management system having a console with a first peristaltic pump rotor and a second peristaltic pump rotor. The cassette comprises a housing, a first flexible tube located in the housing, and a second flexible tube also located within the housing. The first flexible tube is configured to engage the first peristaltic pump rotor when the cassette is mounted on the console, and the second flexible tube is configured to engage the second peristaltic pump rotor when the cassette is mounted on the console.

The disposable will preferably further include a locking mechanism carried on the housing, which mechanism detachably locks the housing into engagement with the peristaltic pump when the cassette is mounted on the console. In the exemplary embodiments, the locking mechanism includes an alignment element on the housing which engages an alignment component on the console to align the first and second flexible tubes with the first and second rotors as the cassette is mounted on the console. More specifically, the alignment element on the housing may comprise a slot and the alignment component on the console may comprise a post configured to be received into the slot as the cassette is mounted on the console. Often, the locking mechanism will further include a cam follower structure on the housing which is configured to engage a powered cam on the console to automatically lock the cassette in place as the cassette is mounted on the console.

In other specific embodiments, the disposable cassette may further comprise a sensing window on at least one of the first and second flexible tubes. The at least one sensing window will usually be positioned to align with a sensor on the console when the cassette is mounted on the console. In an exemplary embodiment, the sensing window may comprise a pressure-responsive region formed in a wall of the at least one flexible tube which is positioned to lie proximate a pressure sensor when the cassette is mounted on the console. Typically, the pressure-responsive region will be a thinned wall region of the tube, but could also be a membrane or other wall feature which would be mounted into a hole or an aperture formed within the cassette tube wall.

The disposable cassettes of the present invention may further comprise other features and components, such as electrical components which can be powered by and/or communicated through an electrical contact array formed on the cassette and positioned to make electrical contact with a similar electrical contact array on the console when the cassette is mounted on the console. In specific embodiments, the electrical contact array may include cassette identification or other information which allows the console to recognize the cassette when the cassette is mounted on the console.

In further embodiments, the flexible tubes of the disposable cassette may include loop portions which are configured to be received over the peristaltic pump rotors of the console. In addition to the loop portions, each of the flexible tubes will further comprise a pair of legs which extend outwardly from the housing of the cassette to allow external connection. An inlet tube can be connected at one end to a receive fluid from a fluid source and at another end to deliver fluid to a surgical tool. An outlet tube can be connected to receive fluid from the surgical tool and to deliver the removed fluid to a receptacle.

In one specific embodiment, the loop portions of the first flexible tube and second flexible tube will be located in a plane which is parallel to a plane of the cassette housing. Similarly, the legs may be disposed within another plane which is also parallel to the plane of the cassette housing. In this embodiment, the loop plane will be laterally offset from the leg plane, i.e. displaced in a direction normal to the plane of the cassette. This particular configuration provides a compact structure for the cassette and simplifies engagement with the pump rotors on the console. In a second specific embodiment, the loop portions of the first and second tubes may be nested within a common plane with the legs of each of the first and second flexible tubes lying in the same plane. This is another particularly efficient design for the cassette.

In a second aspect, the present invention provides consoles for use with a tubing cassette having first and second flexible tubes therein. The console will comprise an enclosure having a surface, a first peristaltic pump rotor on the surface and a second peristaltic pump rotor also on the surface. The first peristaltic pump rotor is configured to engage the first flexible tube of the cassette when the cassette is mounted on the console, and the second peristaltic pump rotor is configured to engage the second flexible tube when the cassette is mounted on the console.

The consoles of the present invention will often include a locking mechanism carried on an enclosure for detachably locking the enclosure into engagement with the cassette housing when the cassette is mounted on the console. The locking mechanism typical includes an alignment component on the console configured to engage an alignment element on the cassette housing to align the first and second rotors with the first and second flexible tubes as the cassette is mounted on the console. The alignment element on the housing typically comprises a slot while the alignment component on the console typically comprises a post configured to be received within the slot as the cassette is mounted on the console. The locking mechanism will often further include a powered cam which is configured to engage a cam follower structure on the housing of the cassette to automatically lock the cassette in place as the housing is mounted on the console.

In still other embodiments, the enclosure of the console may have a sensor configured to align with a sensing window on at least one of the first and second flexible tubes of the cassette when the cassette is mounted on the console. The sensor is typically a pressure sensor configured to sense pressure through a pressure-sensing window, which window may be formed as a pressure-responsive region within a wall of at least one of the first and second flexible tubes.

In yet other embodiments, the consoles of the present invention may further comprise an electrical contact array positioned to make electrical contact with an electrical contact array on the cassette housing when the cassette is mounted on the console. The electrical contact arrays may provide a variety of capabilities including power and information transfer between the console and the cassette. In certain embodiments the electrical contact array may provide cassette identification information which allows the console to recognize the cassette when the cassette is mounted on the console.

The console may still further comprise a structure to support and manage fluid being provided to the patient. For example, the console may include an elongate pole configured for hanging a fluid bag and a load sensor adapted to weigh the contents of the fluid bag when it is hung on the pole.

In a third aspect, the present invention provides methods for mounting a tube set on a rotor pump console. The methods comprise providing a tubing cassette having first and second flexible tubes. A rotor pump console is also provided and includes an enclosure with a surface, a first peristaltic pump rotor on the surface, and a second peristaltic pump rotor on the surface. The peristaltic pump rotors are configured to engage the first flexible tube and the second flexible tube when the cassette is mounted on the console.

In preferred aspects, the methods will further comprise detachably locking the enclosure into engagement with the cassette housing when the cassette is mounted on the console. Locking may comprise engaging an alignment component on the console with an alignment element on the cassette to align the first and second rotors with the first and second flexible tubes when the cassette is mounted on the console. Often, a post on the console is inserted into a slot on the cassette in order to effect alignment. Locking may then comprise powering a cam on the console to engage a cam follower structure on the housing in the cassette to automatically lock the cassette in place as the cassette is mounted on the console. These methods may further comprise sensing a condition of a fluid within the tubing set after the tubing set has been mounted on the console. Such sensing will often comprise aligning a sensing window on at least one of the first and second tubes of the cassette with a sensor on the console when the cassette is mounted on the rotor pump console. For example, pressure may be sensed with a pressure sensor through a pressure-sensing window including a pressure-responsive region formed on a wall of at least one of the flexible tubes.

In still other embodiments, electrical contacts may be formed between electrical contact arrays on the cassette and on the console in order to provide power, information, or other electrical signals.

DETAILED DESCRIPTION OF THE INVENTION

Figure 5A:
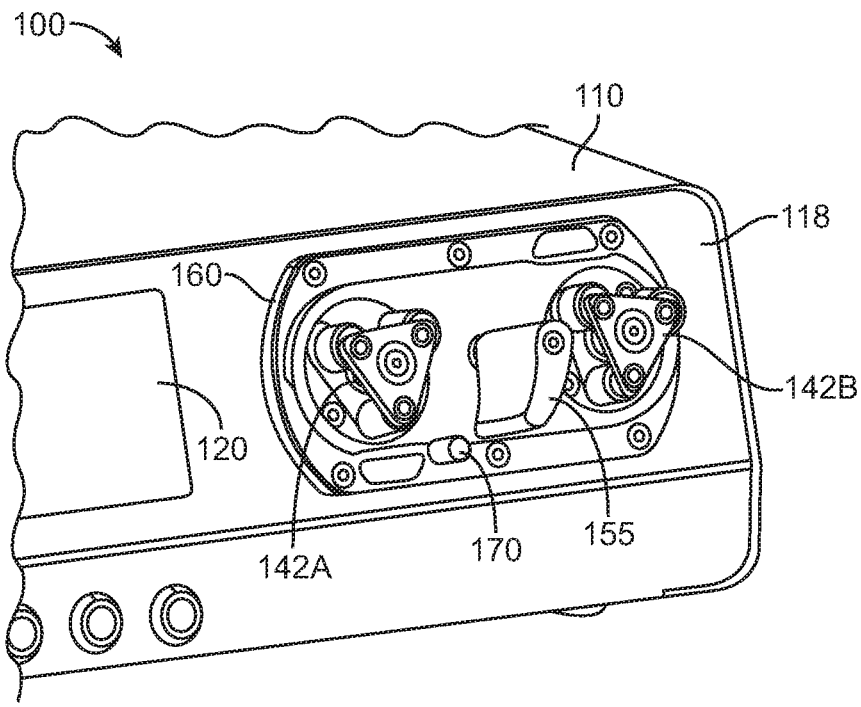
FIG. 5A is a view of a control unit or console before coupling the cassette and tubing set to the control unit.

The fluid management system 100 of the invention includes a disposable cassette 105 (FIGS. 1, 2, 5B) that carries portions of a tubing set and a control unit 110 as shown in FIG. 5A. The fluid management system 100 is used in endoscopic procedures, which can be a urology surgery, gynecology procedure or arthroscopic surgery, to provide inflows and outflows of a pressurized fluid to a working space or body cavity. The fluid can be delivered to provide a pre-set pressure level within the treatment space. The fluid pressure in the space is controlled by control algorithms in the control unit 110, which can monitor pressure in the space or the system 100 and then vary the inflow and/or outflow to maintain the targeted pressure or a targeted pressure and rate of flow.

Figure 3:
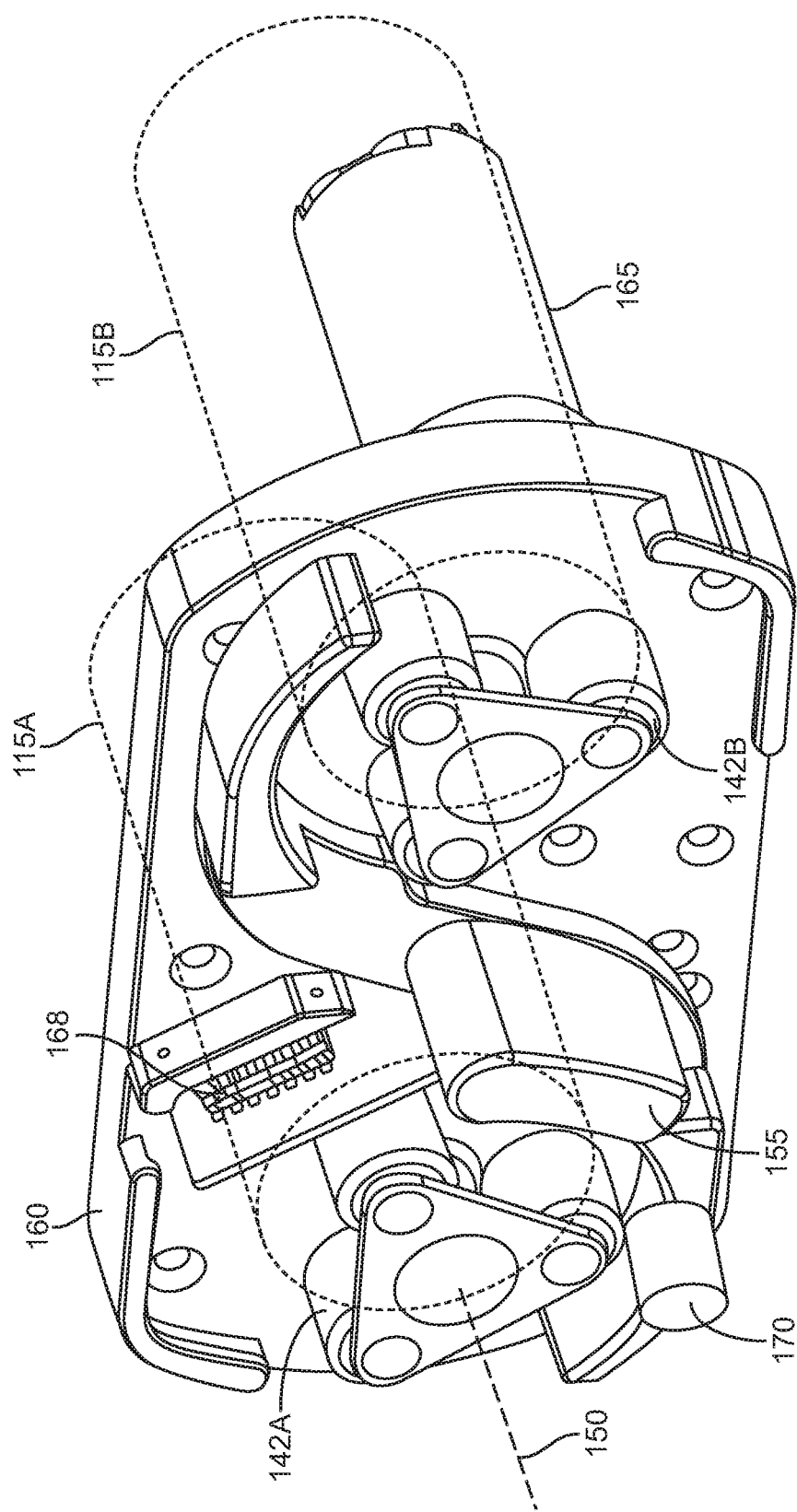
FIG. 3 is a view of a portion of the front of the control unit that shows the roller assemblies of the first and second peristaltic pumps.

Referring to FIGS. 3 and 5A, the console or control unit 110 carries the first and second peristaltic pumps with motors 115A and 115B wherein the first pump provides inflows into a working space and the second pump provides outflows from the working space. Typically, the fluid inflows and outflows are provided through one or more channels in an endoscope. The control unit 110 includes a microprocessor and may further include an RF generator or to other energy source for coupling to a surgical instrument.

In FIG. 5A-5D, one variation of control unit 110 has a front surface 118 including a display that can provide a graphical user interface in the form of a touch-screen interface 120 that permits the operator to control system operations. For example, the touch screen 120 can allow the operator select a target pressure, flow rate or mode of operation. In one variation described further below, the touch-screen 120 can indicate when the user positions the cassette 105 in the correct interface with the control unit 110, and thereafter the control unit can automatically activate a locking motor to engage and move the cassette 105 from a pre-locked position to a locked position. In these steps, the touch-screen 120 can display the pre-locked and locked positions. The touch-screen 120 can then be 'touched' to actuate the locking motor to unlock the cassette 105 following a procedure. In other variations, the cassette 105 can be manually inserted and rotated into a locked positioned in the steps illustrated in FIGS. 5A-5C. It has been found that significant manual force may be required to rotate the cassette 105 into a locked position, and the amount of force may vary depending the orientation of the pump rollers assemblies, and for this reason a motorized locking system is suitable.

Figure 1:
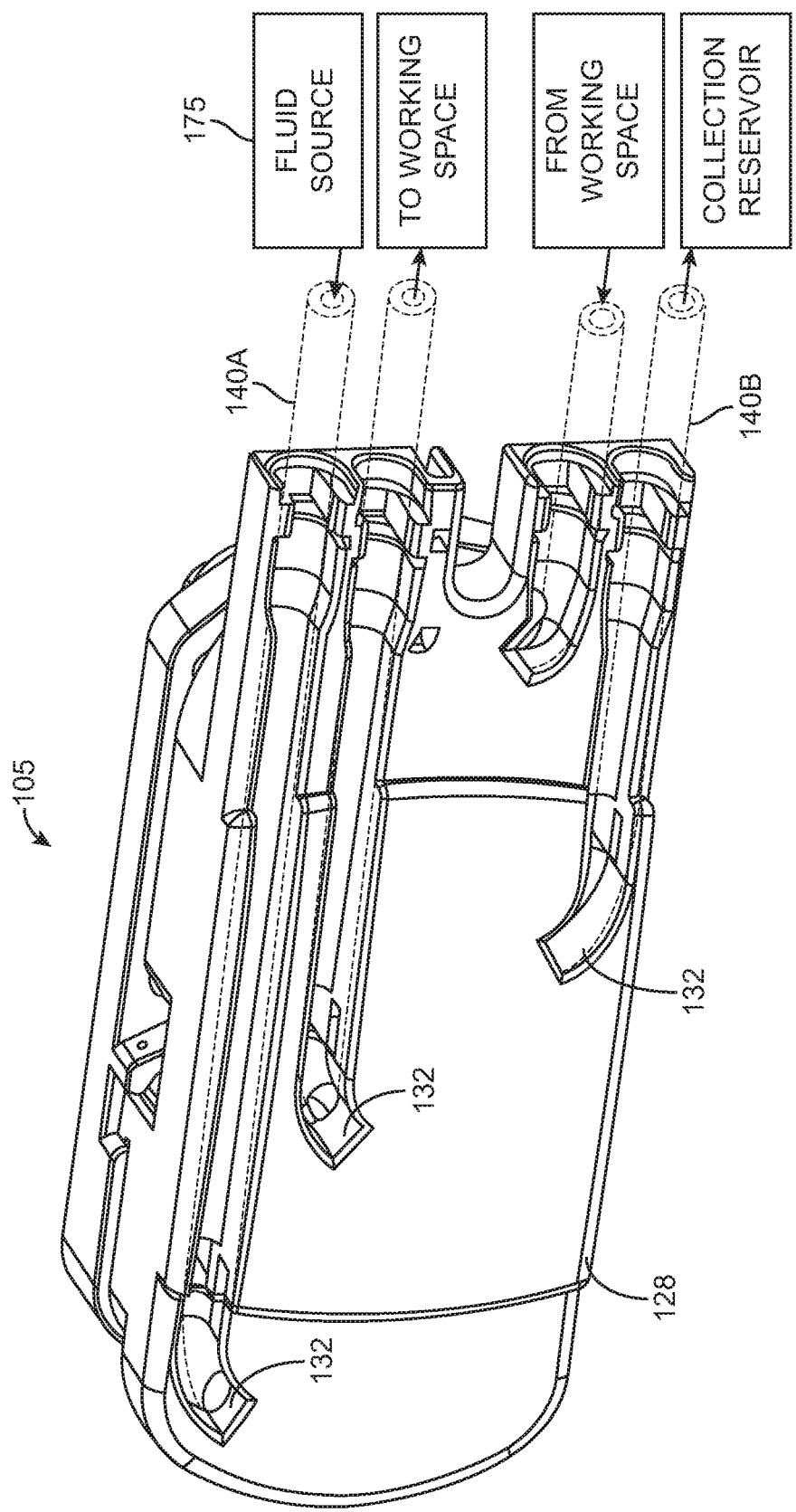
FIG. 1 illustrates a front side of a disposable cassette that carries first and second tubes adapted to mate with a first (inflow) peristaltic pump and a second (outflow) peristaltic pump within a control unit.
Figure 2:
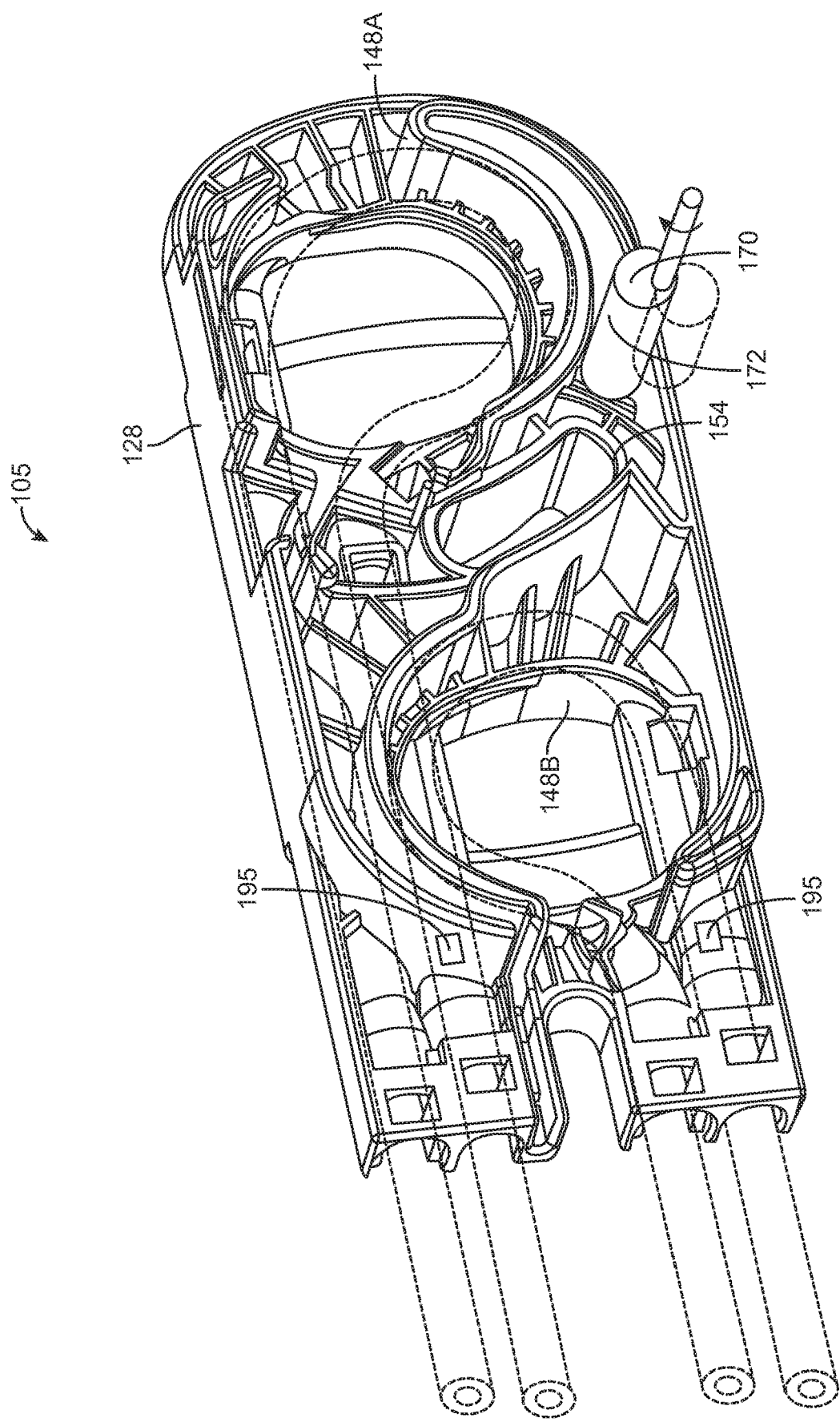
FIG. 2 illustrates a back side of the cassette of FIG. 1.

Referring to FIGS. 1 and 2, the cassette 105 includes a plastic molded housing or body 128 that has molded pathways 132 for receiving and retaining portions of a tubing set, and more particularly of a portion of a flexible inflow tube 140A and a portion of an outflow tube 140B. These tubes are typically polymer tubing having a diameter ranging between about ¼" to ½" and are adapted to operate with the first and second roller assemblies 142A and 142B of pumps 115A and 115B (see FIGS. 3 and 5A). The tube portions 148A and 148B within the cassette (see FIG. 2) extend in a semicircular arc of at least 90° or at least 120° in a plane within the cassette, with the plane adapted to be aligned with the plane P of the first and second roller assemblies 142A and 142B as shown in FIG. 7, that is, perpendicular to the axis 150 of a shaft of a peristaltic pump 115A or 115B (FIGS. 3 and 7). The cassette 105 has a central slot 154 that mates with a projecting element 155 on the control unit 110 to align the cassette with the roller assemblies 142A and 142B when the cassette is pushed onto the control unit 110. In one variation, the cassette 105 can pushed into position in the aforementioned plane P relative to the roller assemblies 142A and 142B, and then rotated in said plane P (FIG. 7) into a final position to engage the tube portions 148A and 148B with the roller assemblies 142A and 142B. In this variation, the tube portions 148A and 148B within the cassette approach and engage the roller assemblies 142A and 142B from different directions, with the rotational axis of the cassette being in the center of the space between the roller assemblies. Any suitable locking mechanism can be used to detachably lock the cassette into the rotated-and-locked position. As can be seen in FIG. 1, the flexible inflow tube 140A has an incoming end in communication with a fluid source such as a saline bag 175 (FIG. 6), and an outgoing end that is coupled to the endoscope or other instrument that delivers fluid to the working space. Similarly, the outflow tube 140B has an incoming end coupled to the endoscope or other instrument that provides an outflow pathway from the working space and outflow end that delivers the outflow fluid to a collection reservoir.

Figure 4:
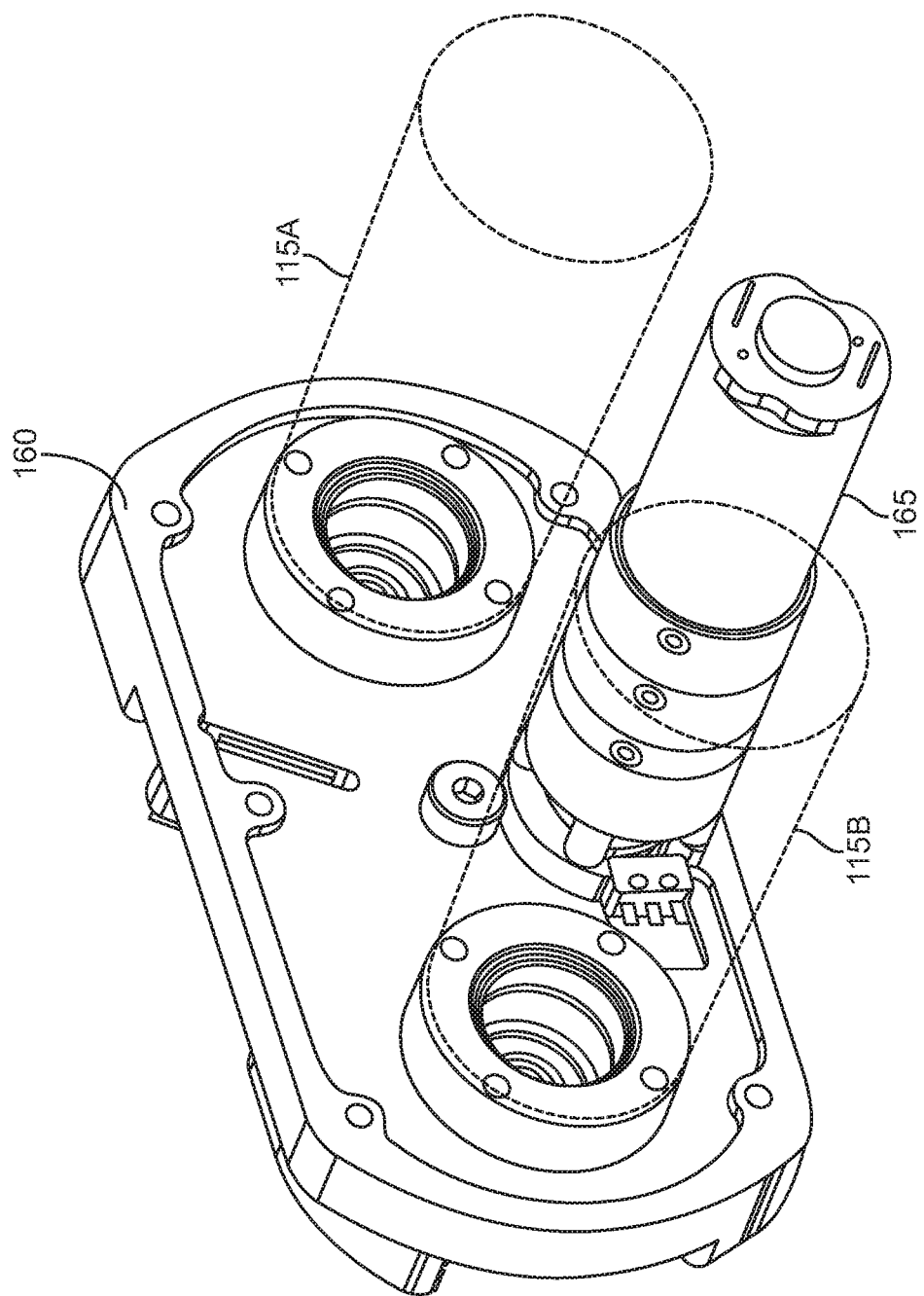
FIG. 4 is a view of the interior or back side of a panel in the control unit showing a motor that is configured to move the cassette from a pre-locked position into a locked position.

Now turning to FIGS. 3 and 4, a panel component 160 from the front panel of the control unit 110 is shown to which the first and second pumps 115A and 115B fastened. The first and second roller assemblies 142A and 142B and pump motors 115A and 115B (phantom view) are shown. In this variation another motor 165 is shown (FIGS. 3 and 4) that is adapted to rotate and lock the cassette into a locked position engaging the tubing set with the roller assemblies 142A and 142B. FIG. 3 further illustrates an electrical contact component 168 and microswitch that is contacted by the cassette 105 when it is pushed toward the front surface of the control unit 110. When the electrical contact component 168 and microswitch is actuated, then the locking motor 165 is activated which in one variation rotates a cam element 170 carried by the panel component 160 (FIGS. 2 and 5A) which rotates and in turn pushes on a molded feature 172 in the back of the cassette 105 (see FIG. 2) to rotate the cassette 105 into a locked position.

Figure 5B:
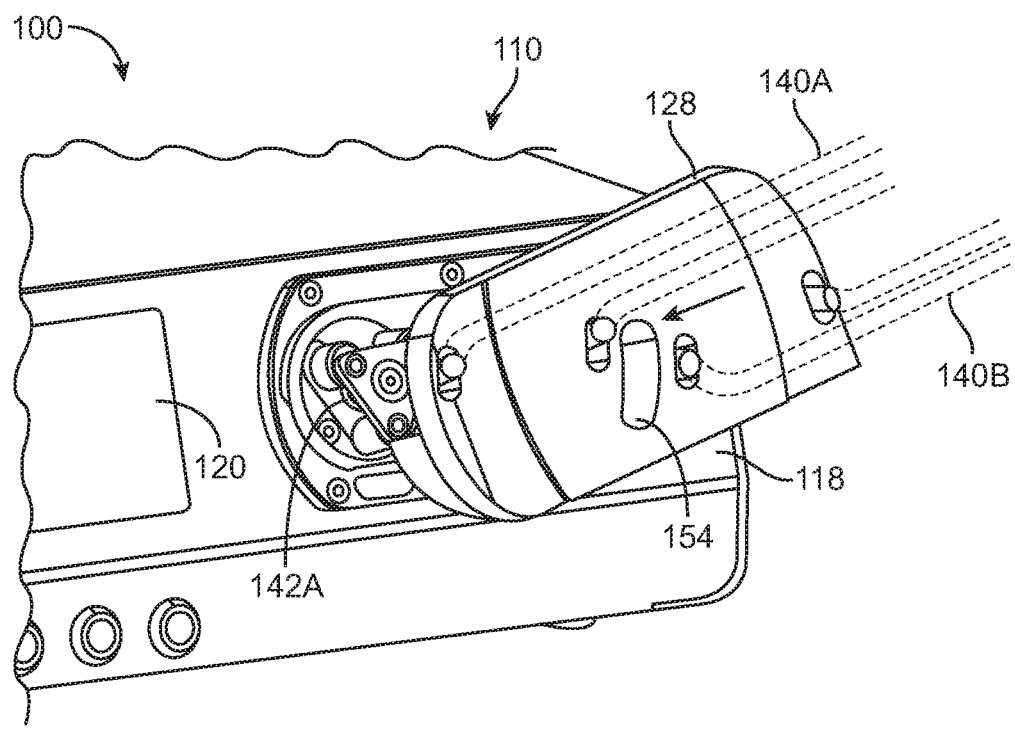
FIG. 5B is a view of the control unit of FIG. 5A with the cassette in sectional view being positioned to couple to the unit.
Figure 5C:
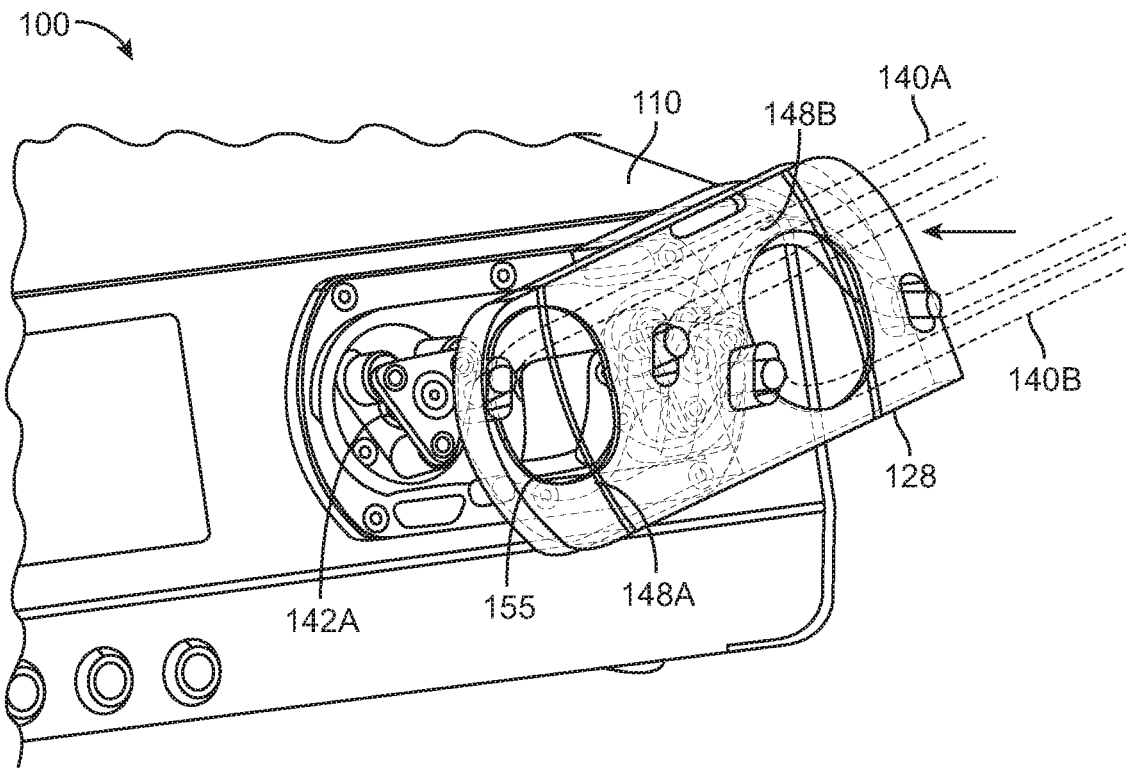
FIG. 5C is a view similar to that of FIG. 5B with the cassette in a transparent view to show the configuration of inflow and outflow tubes within the cassette.
Figure 5D:
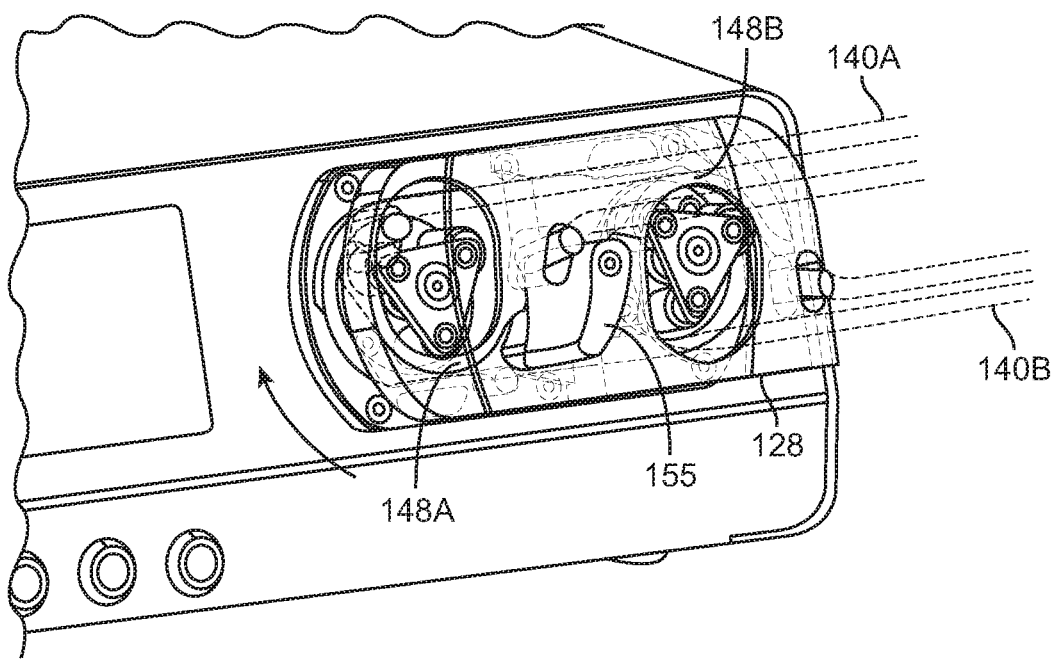
FIG. 5D is a view of the cassette in a transparent view being rotated from a pre-locked position into a locked position in the control unit.

FIGS. 5A-5D show the sequence of coupling the cassette 105 with the control unit 110. In FIGS. 5A and 5B, the cassette is being positioned to be pushed inward toward the front panel of the control unit 110. In FIG. 5C, the transparent view of the cassette 105 show the portions of inflow and outflow tubes 148A and 148B in a semi-circle for engagement with the first and second roller assemblies 142A and 142B. Finally, FIG. 5D shows cassette 105 after being rotated from a pre-locked position into a locked position in the control unit 110.

Figure 6:
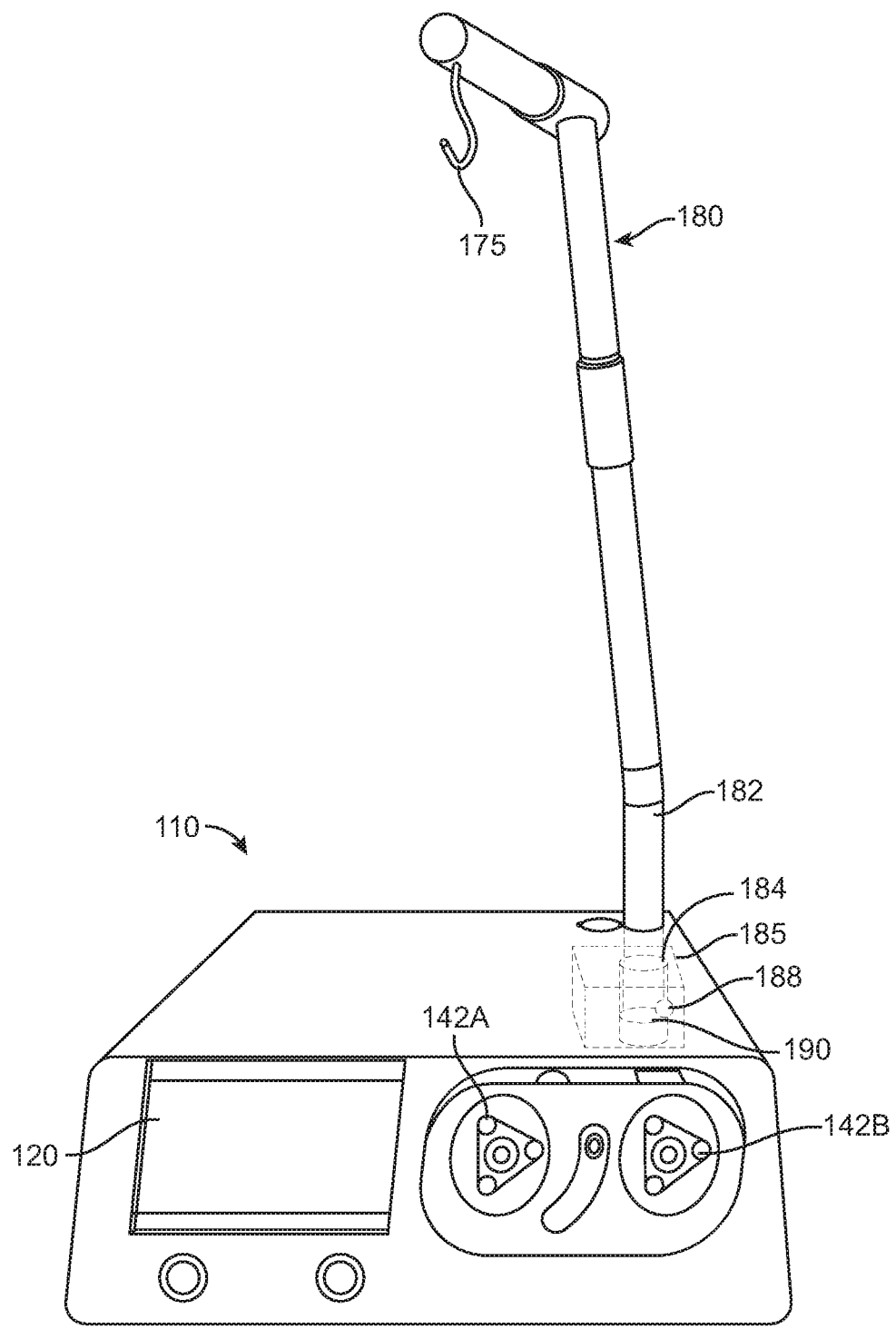
FIG. 6 is a perspective view of a control unit including a pole for hanging a fluid source and a load sensor for monitoring the volume of remaining fluid during a procedure.
Figure 7:
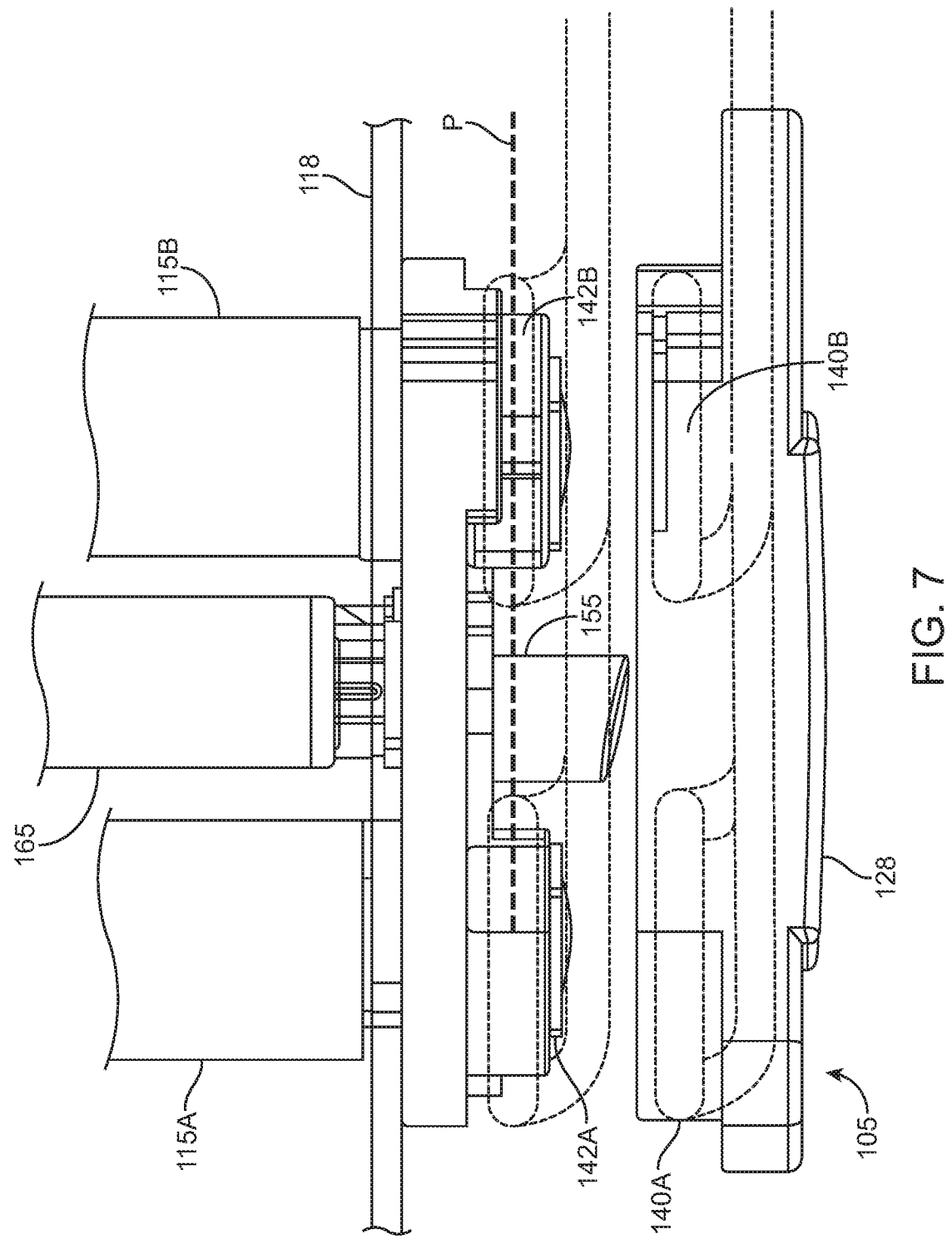
FIG. 7 is a top view of a cassette showing the tubing configuration in the cassette to allow for alignment and engagement of the tubing with the roller assemblies of the pumps.

FIG. 6 shows a variation of a control unit 110 of the invention that includes a pole 180 for hanging a fluid sac reservoir or sac 175 therefrom at a fixed height above the unit. In one variation, the pole has a base portion 182 that can be inserted into a mating bore 184 is a block 185 within the control unit 110. The base of the pole base portion 182 and receiving bore 184 are provided with a sensor 188 to indicate to the control unit 110 that the pole is properly installed. At the base of the pole 180 and block 185 is a load sensor 190 that is capable of measuring the weight of the fluid in the reservoir 175. The load sensor 190 is operatively coupled to the controller microprocessor and algorithms can be provided to alert the user of a fluid deficit (and fluid overload in the patient) which is very important in urology and gynecology procedures. The load sensor 190 can initially set the control unit 110 for a procedure by signaling what volume of fluid sac 175 is being used (e.g., a 3 liter or 5 liter saline sac). The control unit 110 can provide a visual and/or audible alert to the operator, for example through the touch screen 120, as to fluid remaining the sac 175 during any procedure.

In FIG. 2, in one variation of cassette 110, one or more pressure sensors 195 can be provided to interface with either or both the inflow and outflow tubing to sense fluid pressure in the tube. An electrical connection for operating such sensors can be provided through the electrical contact component 168 shown in FIG. 3 which contacts exposed electrical leads in mating component 205 in the cassette 105 (see FIG. 8) as further described below.

The electrical contacts component 168 as shown in FIG. 3 also can comprise a cassette recognition mechanism wherein features on the cassette together with microswitches coupled to the electrical contact component 168 can recognize different types of cassette that have been locked in place and also can recognize that a cassette is locked properly in place. Alternatively, the control unit 110 can utilize a wireless sensor to signal the control unit as to the presence and the type of a cassette.

FIG. 7 shows a top view of the cassette and indicates how portions of the tubing 140A and 140B are shaped and held in channels 132 in the cassette 105 to mate with the roller assemblies 142A and 142B of the control unit 110.

Figure 8:
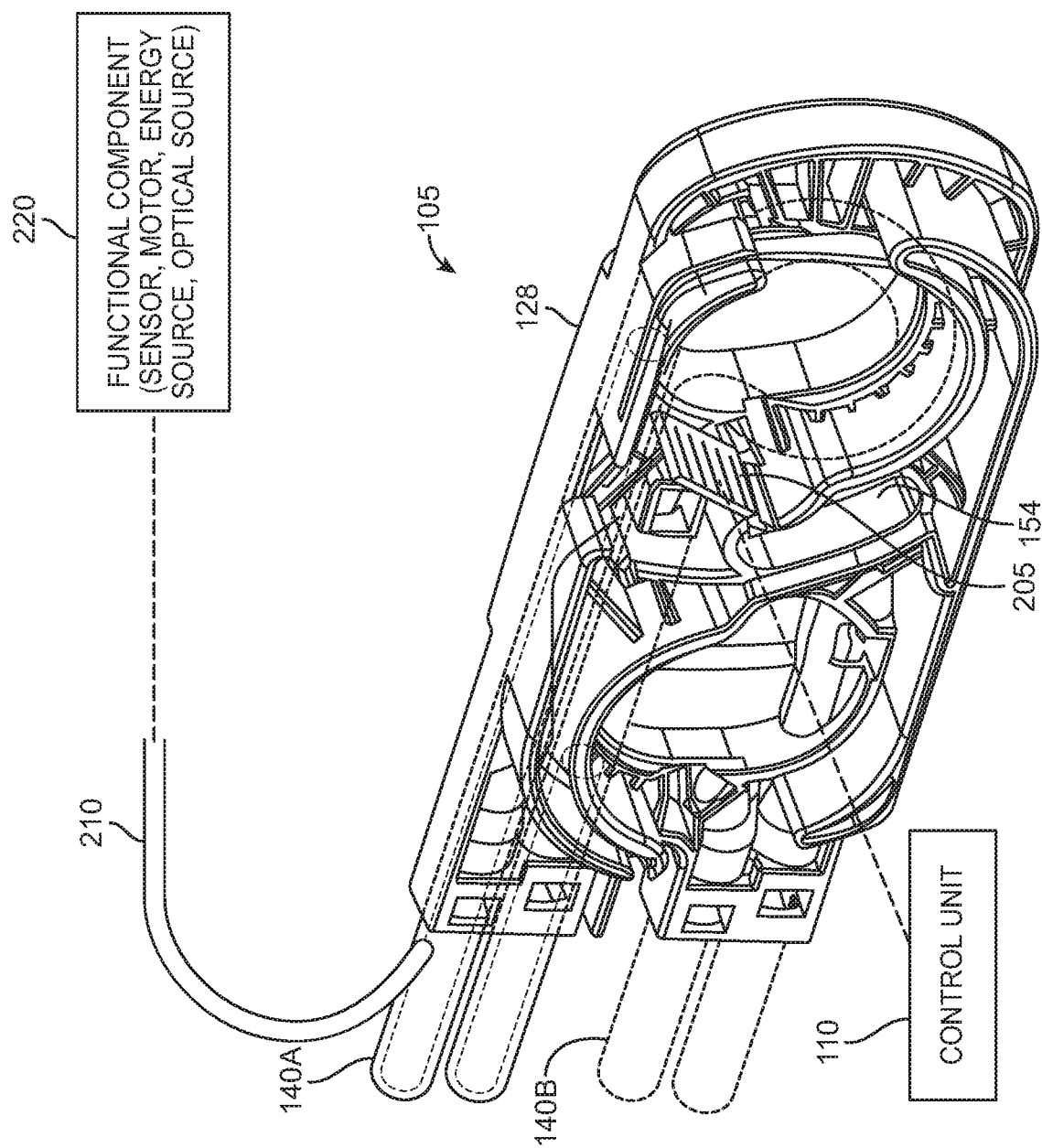
FIG. 8 is another view of the back of the cassette of FIGS. 1-2 showing a connector element.

FIG. 8 shows the back of cassette 105 with a view of the contact or connector component 205 that is adapted to contact and engage the control unit's electrical contact component 168. When viewing FIGS. 3 and 8, it can be understood that the contact components 168 and 205 cah ave from 2 to 20 or more independent electrical contacts which can complete electrical circuits to enable or energize various functions. FIG. 8 shows that an electrical cable 210 can extend from the connector component 205 and tubing 140A to a functional device or system, such as a motor or a sensor.

In one variation, the cable 210 can have one or more electrical leads to all operation of an electrical motor in a tissue resecting device. In another variation, the cable 210 can be operatively coupled to a sensor, for example within the group of temperature sensors, pressure sensors, flow rate sensors, flow volume sensors, impedance sensors, capacitance sensors, voltage sensors, atmospheric pressure sensors, accelerometer sensors, tilt sensors, CCDs, optical sensors and rpm sensors.

In another variation, the first and second connector components 168 and 205 when coupled can enable or energize an ablation device, a resecting device, a cooling device, a suction device, an irrigation device or a drug delivery device. The aforementioned device may be an RF device, a microwave device, a laser device or a cryofluid device.

In another variation the connector components 168 and 205 of FIGS. 3 and 8 can comprise parts of optical connectors to enable light transmission through the connection.

In general, the system of FIGS. 3 and 8 discloses a medical fluid management system comprising a cassette, a flexible tube within the cassette configured for mating with a pump roller assembly within a control unit; and a first connector component within the cassette adapted for coupling with a second connector component in the control unit for enabling an operating mechanism of the system. The system couples together first and second connector components that when connected provide an electrical connection. In another variation, the first and second connector components when connected provide an optical connection. In another variation, the first and second connector components when connected provide a flow passageway connection which may be useful for operating a pressure sensor.

The system of FIGS. 3 and 8 further includes a locking mechanism for detachably locking the cassette and tubing into a locked position which engages the first and second connector components 168 and 205.

Figure 9:
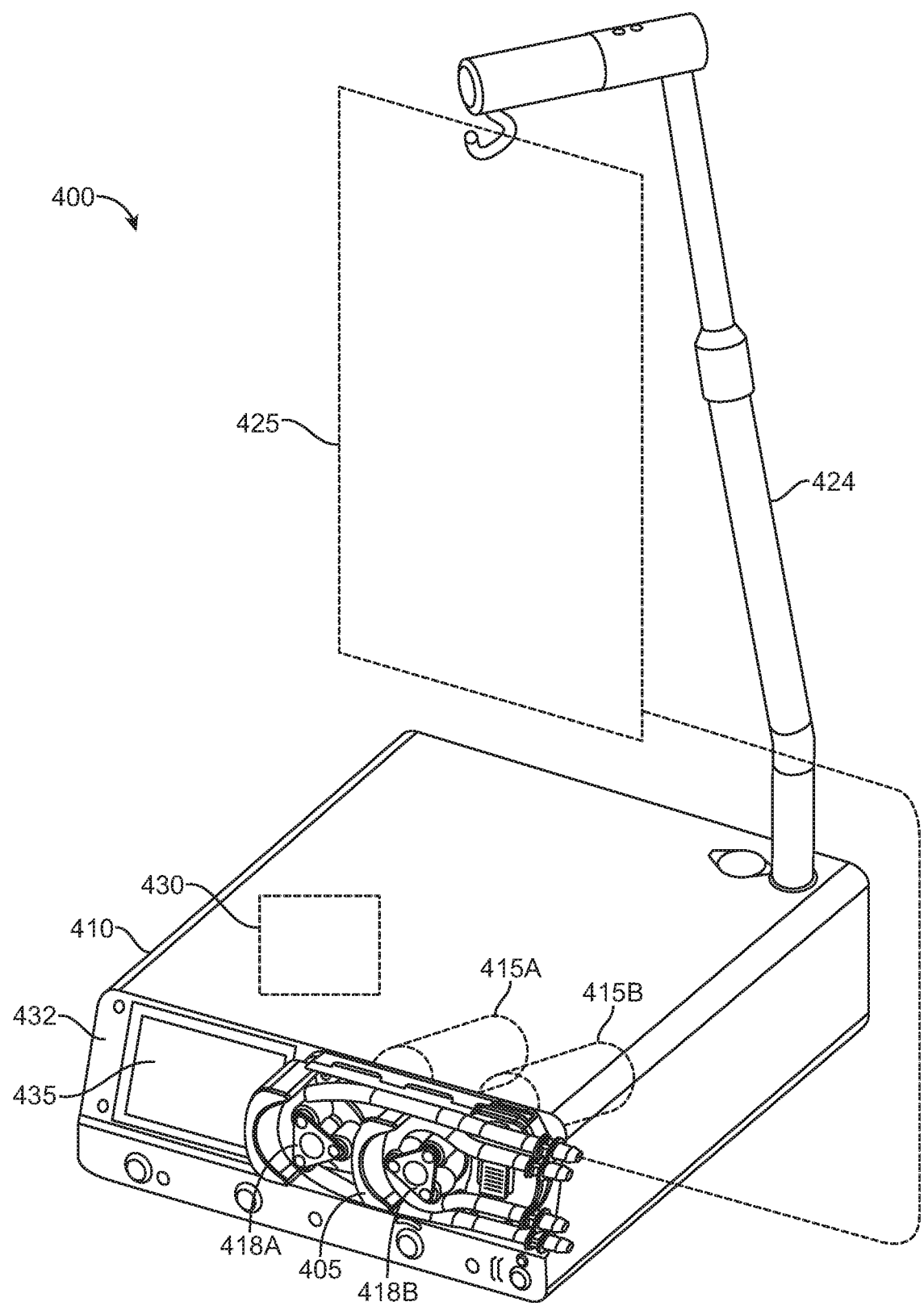
FIG. 9 is perspective view of an embodiment of a fluid management system with a transparent view of a tubing cassette in an operating position on the console.
Figure 10:
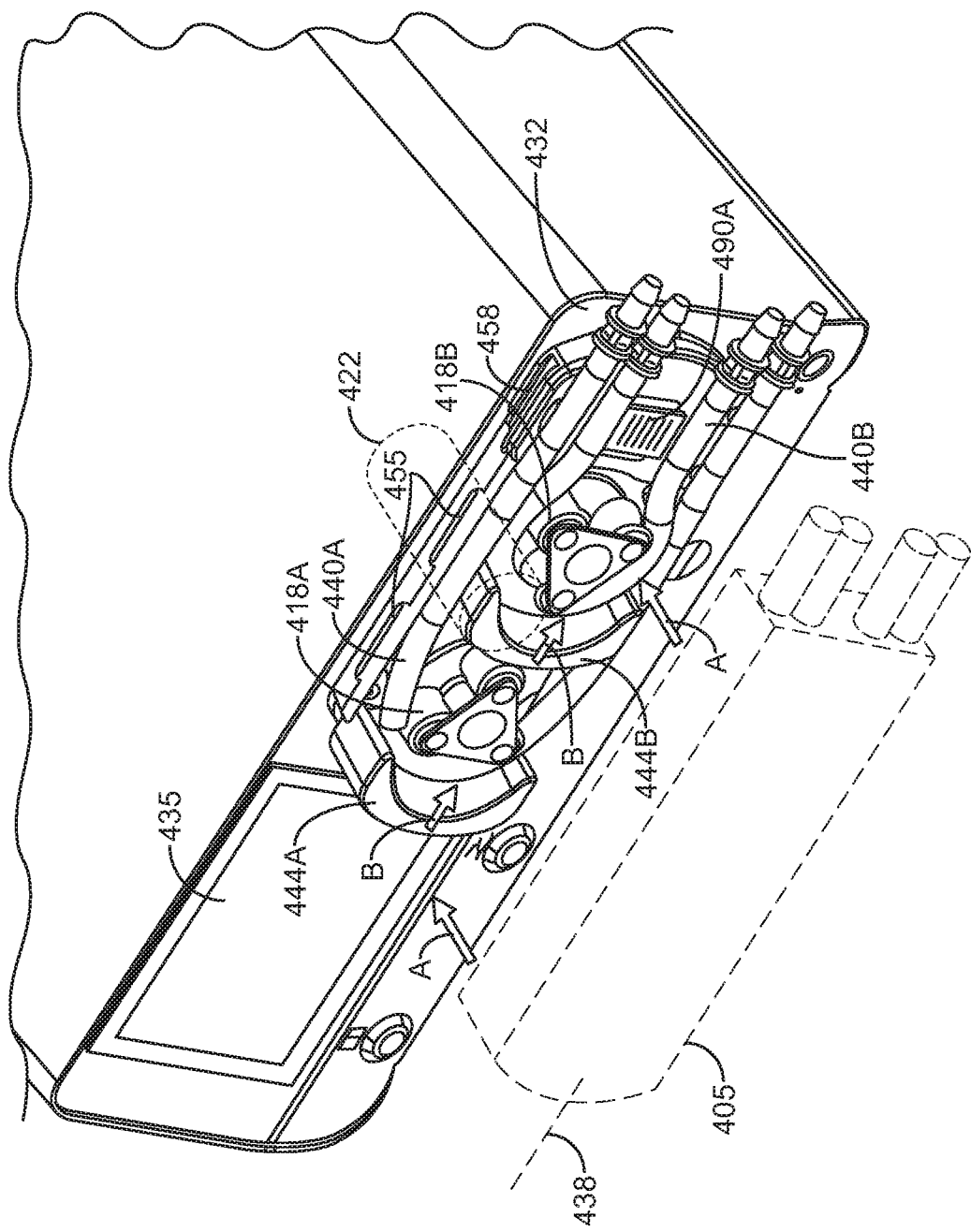
FIG. 10 is close-up view of roller assemblies of dual peristaltic pumps carried by the console of FIG. 9 showing inflow and outflow tubing with the cassette housing removed and components of the console that are motor driven to move the cassette into an operating position.
Figure 11:
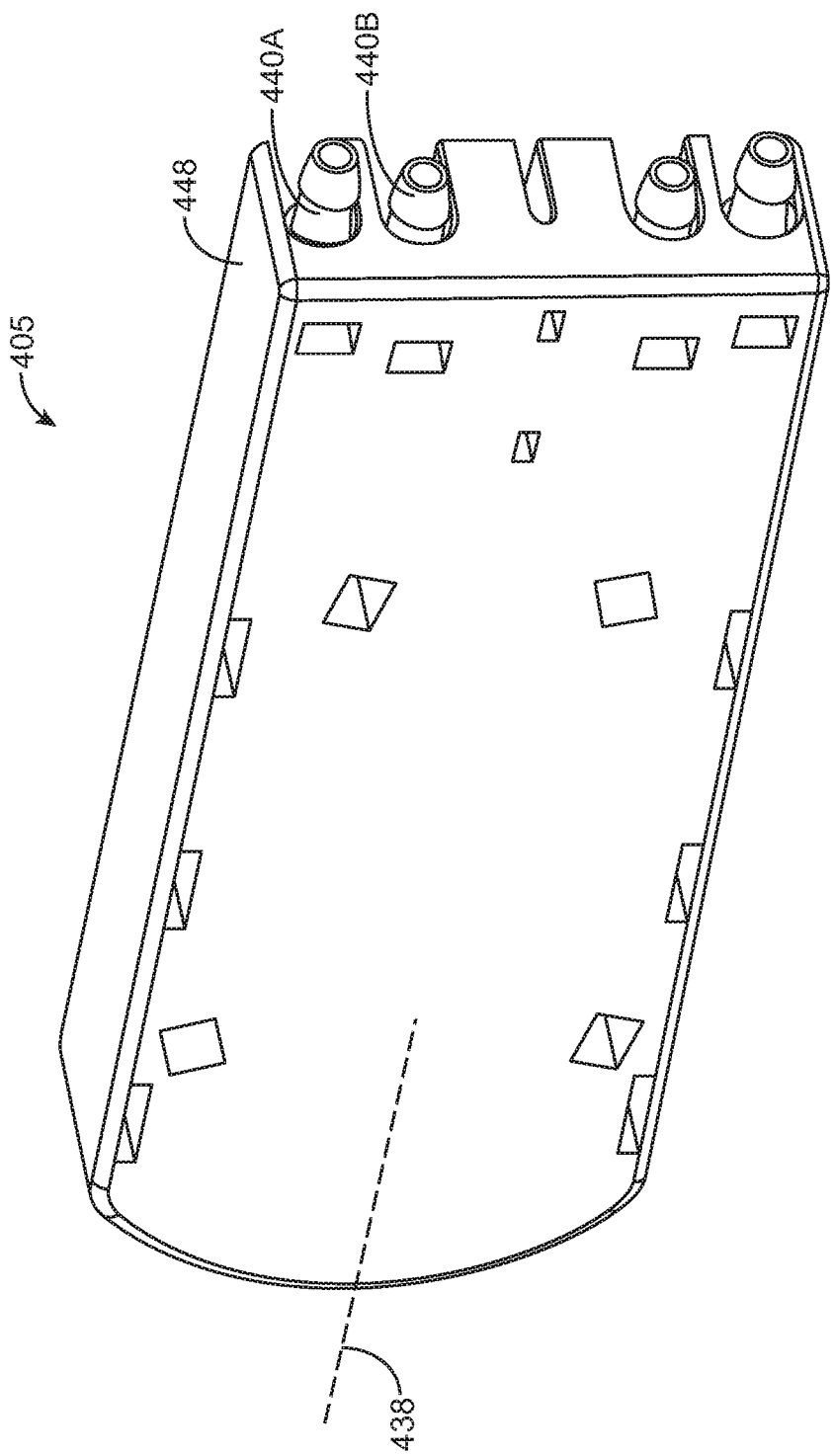
FIG. 11 is view of the front of the cassette of FIGS. 9-10.

FIGS. 9-10 illustrate another embodiment of fluid management system 400 which includes a disposable cassette 405 that again carries portions of a tubing set. The system 400 further includes a control unit or console 410 which carries first and second peristaltic pumps 415A and 415B which have exposed and accessible pump roller assemblies 418A and 418B in the front panel of the console. In this variation, the console again carries a motor 422 shown in FIG. 10 that is adapted to engage and move the cassette 405 into an operating position that engages the tubing set in the cassette 405 with the pump roller assemblies.

As can be seen in FIG. 9, the console 410 includes a pole 424 for carrying a fluid source 425 which can be a saline bag as used in endoscopic surgeries. The pole 424 can be equipped with a load sensor to enable weight-based fluid management as is known in the art to allow a determination of fluid absorption by a patient.

The console 405 carries a control system or controller 430 with microprocessors that operate in accordance with algorithms to control inflows and outflows of a fluid to a working space to maintain a pre-set pressure level within the space. The console 410 can further include an RF generator or other energy source for coupling to a surgical instrument. The system can monitor pressure in a space directly with a pressure sensor in a fluid communication with the space through an open channel in a device which then will allow the controller 430 to vary inflows and/or outflows to maintain the targeted pressure. In another variation, the cassette 405 is configured to interface with console pressure sensors as will be describe below to sense pressure in the inflow and outflow tubing sets to allow a calculation of pressure in a working space.

In FIGS. 10-12A, a variation of console 410 and cooperating cassette 405 are shown. The console has a front surface 432 including a touch-screen interface 435 that permits the operator to control system operations. In one variation, the touch-screen 435 can be touched to release the cassette 405 after its in an operating position as will be described below.

Figure 12A:
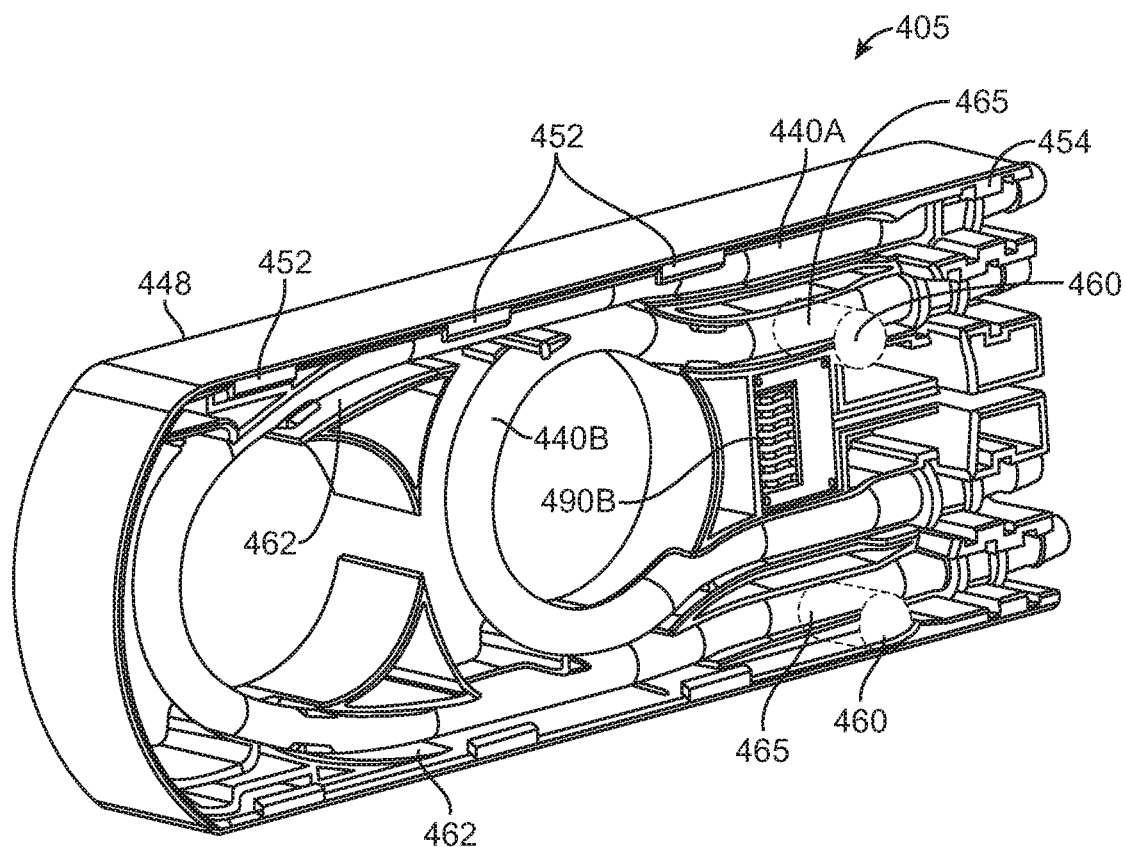
FIG. 12A is view of the back of the cassette of FIG. 10 showing the tubing positioned in the cassette and the location of a tubing sections having a reduced wall thickness to interface with console pressure sensors.
Figure 12B:
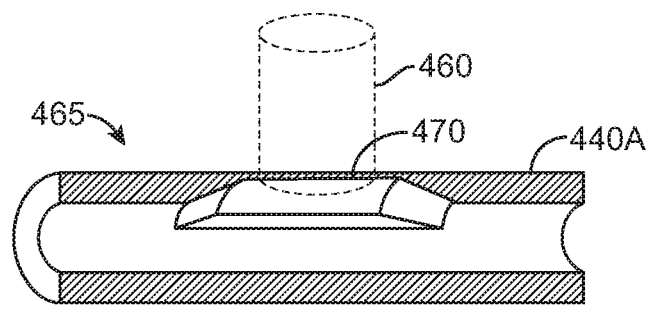
FIG. 12B is a cut-away view of a portion of tubing with a reduced wall thickness that interfaces with a pressure sensor carried in the console.

As can be seen in FIGS. 10 and 12A, the elongate cassette 405 has an axis 438 and is moved in a direction perpendicular to axis 438 (see arrows A) by the user into an interface with the console 410 and the pump roller assemblies 418A and 418B. Thereafter, the motor 422 is actuated to move the cassette 405 and inflow and outflow tubes 440A and 440B into engagement with the pump roller assemblies 418A and 418B. As can be understood from FIG. 10, the semi-circular members or eyebrows 444a and 444b of the console are mounted on a metal plate that is moved in the direction of arrows B relative to the console front surface 432 by the motor 422 driving a cam mechanism. Thus, the movement of the semi-circular members 444a and 444b presses the tubing into engagement with the roller assemblies 418A and 418B. In FIG. 12A, it can be seen that the cassette housing 448 has a plurality of tab elements 452 and 454 that are adapted to slide behind guide elements 455 on the console 410 (FIG. 10) to lock the cassette 405 into a plane at the surface of the console 410. The tab elements 454 of the cassette 405 (FIG. 12A) are adapted to slide into guide track 458 at one side of the console 410 (FIG. 10).

As can be understood from FIG. 10, the motor 422 moves cassette 405 linearly a fixed distance into an operating position wherein the tubes 440A and 440B properly engage the pump rollers 418A and 418B, and in one variation, the plate carrying the semi-circular members 444a and 444b can have spring engagement with the motor-driven cam that holds the cassette in place to allow some slight adjustment in its location during operation. The trigger for the motor 422 to drive the cassette laterally (arrows B in FIG. 10) can be a microswitch that is actuated by the operator inserting the cassette 405 over the pump roller assemblies and into contact with the console front surface, or by pressure sensors 460 described below that can perform multiple functions, and sense initial pressure of the tubing against the sensors.

Referring to FIG. 12A, the cassette 405 includes a plastic molded housing or body 448 that has molded channels 462 for receiving and retaining portions of a inflow tube 440A and outflow tube 440B. The tubing can be maintained in place by adhesives and/or gripping tabs in the molded channels 462.

FIG. 12A also illustrates that the cassette 405 is adapted to have selected portions of the tubing interface with at least one pressure sensor 460 in the console surface 432 for sensing a fluid pressure in either or both tubings 440A and 440B. The locations of the sensors 460 relative to the tubing can be either or both upstream and downstream from the roller assemblies 418A and 418B depending on the application. In FIG. 12A, two sensors 460 are shown in phantom view in the relative position the sensors would be located in the console. In FIG. 12A, two sensors engage tubings 440A and 440B but there can be one to four sensors. Of particular interest, referring to FIG. 12B each portion of tubing 465 that interfaces with a sensor 460 has a reduced thickness wall portion or sensing window 470 that allows for more accurate sensing of fluid pressure than would be possible through a full thickness tubing wall. The wall thickness can be from 5% to 50% of the full wall thickness, or from about 0.02 mm to 1.0 mm in thickness.

FIGS. 10 and 12A further show the contact or connector components 490A and 490B in the console 410 and cassette 405, respectively, that are adapted to contact and engage circuitry components. When viewing FIGS. 10 and 12A, it can be understood that the contact components 490A and 490B can provide up to 20 or more independent electrical contacts which can complete electrical circuits to enable or energize various functions, devices, operations, identifications and the like. In one variation, the contact components 490A and 490B can enable use of an electrical motor and RF delivery circuitry in a tissue resecting device. In another variation, the contacts can be operatively coupled to a sensor, for example, within the group of temperature sensors, pressure sensors, flow rate sensors, flow volume sensors, impedance sensors, capacitance sensors, voltage sensors, atmospheric pressure sensors, accelerometer sensors, tilt sensors, CCDs, optical sensors and rpm sensors that may be useful in operating a medical device.

In general, a cassette corresponding to the invention is adapted for use in a surgical fluid management system and comprises a housing carrying at least one flexible tube configured to engage a roller assembly of a peristaltic pump. The disposable cassette also comprises a housing carrying at least one contact surface for contacting a cooperating motor driven surface of a console for moving the cassette with a motor drive into an operating position. Further, the disposable cassette comprises a housing carrying at least one flexible tube and a guide element configured to cooperate with a console guide track for guiding the cassette from an initial non-operating position into an operating position.

In another aspect of the invention, a disposable cassette for use in a surgical fluid management system comprises a housing carrying at least one flexible tube having a tubing portion with a reduced thickness wall for interfacing with a sensor carried within a cooperating console. The disposable cassette also comprises a housing carrying at least one flexible tube and a mechanism component for cooperating with a console component to provide a signal that the cassette is positioned in an operating position in the console.

In another aspect of the invention, a disposable tubing cassette comprises an elongated housing extending along a first axis and a sensor mechanism component adapted to cooperate with a console component to signal when the cassette is moved in the direction of a second axis transverse to the first axis into a position proximate the surface of a console.

In another aspect of the invention, a disposable cassette and console include an identification mechanism for allowing a controller to identify the type of cassette when engaged with the console. In another aspect of the invention, a disposable cassette and console include at least one enabling mechanism for enabling the activation of fluid management system, medical device, sensor or other function.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A disposable cassette for use with a surgical fluid management system having a console with a first peristaltic pump rotor and a second peristaltic pump rotor, said cassette comprising:
a housing;
a first flexible tube located in the housing and having a loop portion which is configured to engage and be received over the first peristaltic pump rotor and a pair of legs which extend outwardly from the housing to allow external connection when the cassette is mounted on the console; and
a second flexible tube located in the housing and having a loop portion which is configured to engage and be received over the second peristaltic pump rotor and a pair of legs which extend outwardly from the housing to allow external connection when the cassette is mounted on the console;
wherein the housing defines a central plane, wherein the loop portions of the first and second flexible tubes are disposed in a loop plane parallel to the central plane, wherein the pair of legs of the first and second flexible tubes are disposed in a leg plane parallel to the central plane, and wherein the loop plane and the leg plane are offset from each other in a direction normal to the central plane.

2. A disposable cassette as in claim 1, further comprising a locking mechanism carried by the housing for detachably locking the housing into engagement with the first and second peristaltic pump rotors when the cassette is mounted on the console.

3. A disposable cassette as in claim 1, wherein the locking mechanism includes an alignment element on the housing which engages an alignment component on the console to align the first and second flexible tubes with the first and second rotors as the cassette is mounted on the console.

4. A disposable cassette as in claim 3, wherein the alignment element on the housing comprises a slot and the alignment component on the console comprises a post configured to be received into the slot as the cassette is mounted on the console.

5. A disposable cassette as in claim 4, wherein the locking mechanism includes a cam follower structure on the housing which is configured to engage a powered cam on the console to automatically lock the cassette in place as the cassette is mounted on the console.

6. A disposable cassette as in claim 1, further comprising a sensing window on at least one of the first and second flexible tubes, wherein the at least one sensing window is positioned to align with a sensor on the console when the cassette is mounted on the console.

7. A disposable cassette as in claim 6, wherein the sensing window comprises a pressure-responsive region formed in a wall of the at least one flexible tube which is positioned to lie proximate a pressure sensor when the cassette is mounted on the console.

8. A disposable cassette as in claim 1, further comprising an electrical contact array on the cassette housing positioned to make electrical contact with an electrical contact array on the console when the cassette is mounted on the console.

9. A disposable cassette as in claim 8, wherein the electrical contact array includes cassette identification information which allows the console to recognize the cassette when the cassette is mounted on the console.

10. A disposable cassette as in claim 1, wherein the loop portions of the first and second flexible tubes are nested within a common plane with the legs of each of the first and second flexible tubes.

11. A console for use with a unitary tubing cassette having first and second flexible tubes, said console comprising:
an enclosure having a surface;
a first peristaltic pump rotor on the surface configured to engage the first flexible tube when the cassette is mounted on the console; and
a second peristaltic pump rotor on the surface configured to engage the second flexible tube when the cassette is mounted on the console;
wherein the first peristaltic pump rotor and the second peristaltic pump rotor are configured to engage a loop portion of the first flexible tube and a loop portion of the second flexible tube, wherein the loop portions of the first and second flexible tubes are disposed in a loop plane parallel to a central plane of the cassette, wherein a pair of legs of the first and second flexible tubes are disposed in a leg plane parallel to the central plane, and wherein the loop plane and the leg plane are offset from each other in a direction normal to the central plane.

12. A console as in claim 11, further comprising a locking mechanism carried by the enclosure for detachably locking the enclosure into engagement with a cassette housing when the cassette is mounted on the console.

13. A console as in claim 12, wherein the locking mechanism includes an alignment component on the console configured to engage an alignment element on the cassette housing to align the first and second flexible rotors with the first and second tubes as the cassette is mounted on the console.

14. A console as in claim 13, wherein the alignment element on the housing comprises a slot and the alignment component on the console comprises a post configured to be received into the slot as the cassette is mounted on the console.

15. A console as in claim 14, wherein the locking mechanism includes a powered cam which is configured to engage a cam follower structure on the housing of the cassette to automatically lock the cassette in place as the cassette is mounted on the console.

16. A console as in claim 11, further comprising a sensor configured to align with a sensing window in at least one of the first and second flexible tubes of the cassette when the cassette is mounted on the console.

17. A console as in claim 16, wherein the sensor is a pressure sensor configured to sense pressure through a sensing window including a pressure-responsive region formed in a wall of the at least one flexible tube which is positioned to lie proximate a pressure sensor when the cassette is mounted on the console.

18. A console as in claim 11, further comprising an electrical contact array positioned to make electrical contact with an electrical contact array on the cassette housing when the cassette is mounted on the console.

19. A console as in claim 18, wherein the electrical contact array on the cassette includes cassette identification information which allows the console to recognize the cassette when the cassette is mounted on the console.

20. A console as in claim 11, further comprising an elongate pole coupled to the enclosure configured for hanging a fluid bag and a load sensor adapted to weigh contents of the fluid bag.

21. A console as in claim 11, wherein the first peristaltic pump rotor and the second peristaltic pump rotor are configured to engage a loop portion of the first flexible tube and a loop portion of the second flexible tube, wherein the loop portions of the first and second flexible tubes are nested within a common plane with the legs of each of the first and second flexible tubes.

\* \* \* \* \*